(12) United States Patent
Millet (10) Patent No.: US 10,512,615 B1
(45) Date of Patent: Dec. 24, 2019

(54) COMPOSITIONS AND METHODS FOR DELIVERING CANNABIDIOL AND KETONE BODIES

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 0 days.

(21) Appl. No.: 16/272,359

(22) Filed: Feb. 11, 2019

Related U.S. Application Data (60) Provisional application No. 62/769,412, filed on Nov. 19, 2018, provisional application No. 62/760,430, filed on Nov. 13, 2018, provisional application No. 62/723,274, filed on Aug. 27, 2018.

(51) Int. Cl.
| | | |
|---|---|---|
| A61K 31/05 | (2006.01) | |
| A61K 47/10 | (2017.01) | |
| A61K 47/14 | (2017.01) | |
| A61P 43/00 | (2006.01) | |
| A61K 31/19 | (2006.01) | |

(52) U.S. Cl.
CPC .............. *A61K 31/05* (2013.01); *A61K 47/10* (2013.01); *A61K 47/14* (2013.01); *A61P 43/00* (2018.01); *A61K 31/19* (2013.01)

(58) Field of Classification Search
CPC ........ A61K 31/05; A61K 47/10; A61K 47/14; A61K 31/19; A61P 43/00
See application file for complete search history.

(56) References Cited

U.S. PATENT DOCUMENTS

| | | |
|---|---|---|
| 2,238,149 A | 4/1941 | Aeckerle |
| 5,093,044 A | 3/1992 | Wretlind |
| 6,207,856 B1 | 3/2001 | Veech |
| 6,316,038 B1 | 11/2001 | Veech |
| 6,323,237 B1 | 11/2001 | Veech |
| 6,613,356 B1 | 9/2003 | Vlahakos |
| 7,351,736 B2 | 4/2008 | Veech |
| 8,101,653 B2 | 1/2012 | Veech |
| 8,124,589 B2 | 2/2012 | Henderson |
| 8,426,468 B2 | 4/2013 | Henderson |
| 8,642,654 B2 | 2/2014 | Clarke et al. |
| 9,138,420 B2 | 9/2015 | D'Agostino et al. |
| 9,211,275 B2 | 12/2015 | Clarke et al. |
| 9,675,577 B2 | 6/2017 | D'Agostino et al. |
| 9,795,580 B2 | 10/2017 | Weeber et al. |
| 2001/0041736 A1 | 11/2001 | Veech |
| 2005/0129783 A1 | 6/2005 | McCleary |
| 2008/0287372 A1 | 11/2008 | Henderson |
| 2009/0253781 A1 | 10/2009 | Veech |
| 2010/0041751 A1 | 2/2010 | Henderson |
| 2001/0197758 | 8/2010 | Andrews et al. |
| 2010/0298294 A1 | 11/2010 | Clarke |
| 2012/0071548 A1 | 3/2012 | Veech |
| 2013/0079406 A1 | 3/2013 | Veech |
| 2017/0296501 A1 | 10/2017 | Lowery et al. |

FOREIGN PATENT DOCUMENTS

| | | |
|---|---|---|
| CN | 1347319 | 5/2002 |
| EP | 2283834 | 2/2011 |
| JP | 11060434 | 3/1999 |
| JP | 2002521330 | 7/2002 |
| RU | 2345546 | 4/2008 |
| WO | WO 98/41200 | 9/1998 |
| WO | WO 03/070823 | 8/2003 |
| WO | WO2005107724 | 11/2005 |
| WO | WO2007115282 | 10/2007 |
| WO | WO2008005818 | 1/2008 |
| WO | WO 2008/021394 | 2/2008 |
| WO | WO 2008/024408 | 2/2008 |
| WO | WO2011101171 | 8/2011 |
| WO | WO 2014153416 | 9/2014 |
| WO | WO 2017/208217 | 12/2017 |

OTHER PUBLICATIONS

Haywood A, Glass BD. Pharmaceutical excipients—where do we begin? Australian Prescriber. 2011; 34: 112-114.
Dolson, Laura. How to Test Your Blood for Ketones. Downloaded Apr. 1, 2015. http://lowcarbdiets.about.com/od/KetogenicDiets/a/How-to-Test-Blood-For-Ketones.htm.
Nova Max Plus Glucose and Ketone Testing with One Monitor. Downloaded Apr. 1, 2015. http://www.novacares.com/nova-max-plus/.
Serum Ketones Test. MedlinePlus Medical Encyclopedia. Downloaded Apr. 1, 2015. http://www.nlm.nih.gov/medlineplus/ency/article/003498.htm.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.
A New Toy Measuring Blood Ketones. Diet Doctor, Aug. 21, 2012. Dowloaded Apr. 1, 2015. http://www.dietdoctor.com/a-new-toy-measuring-blood-ketoones.
Precision Xtra vs. NovaMax Plus: Ketone Meter Evaluation. Jimmy Moore's Livin' La Vida Low Carb Blog. Downloaded Apr. 1, 2015. http://livinlavidalowcarb.com/blog/precision-xtra-vs-novamax-plus-ketone-meter-evaluation/15918.
Kirsch, Jr et al. "Butanediol Induced Ketosis Increases Tolerance to Hypoxia in the Mouse." Stroke. 1980, vol. 11, No. 5, pp. 506-513.

(Continued)

*Primary Examiner* — Sahar Javanmard
(74) *Attorney, Agent, or Firm* — Workman Nydegger (57) ABSTRACT

Disclosed herein are "ketonnabidiol" compositions including a combination of: (1) cannabidiol (CBD) and/or cannabidiolic acid (CBDA); (2) a ketone body component such as beta-hydroxybutyrate (BHB) and/or acetoacetate; and (3) a dietetically or pharmaceutically acceptable carrier. Also disclosed herein are methods of using such ketonnabidiol compositions for producing desired physiological effects, such as fat loss, in a mammal. The ketonnabidiol compositions beneficially enhance fat loss through ketosis while also reducing the duration and/or severity of unpleasant "keto flu" symptoms typically associated with ketosis.

24 Claims, 1 Drawing Sheet

(56) References Cited

OTHER PUBLICATIONS

Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.

Henderson, Samuel T. "Ketone Bodies as a Therapeutic for Alzheimer's Disease." Neurotherapeutics. Jul. 2008;5 3 3):470-80.

Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.

Krotkiewski, M. "Value of VLCD Supplementation with Medium Chain Triglycerides." I'nt J Obes Relat Metab Disord. Sep. 2001;25(9):1393/\00.

PCT International Search Report and Written Opinion issued by the International Searching Authority dated Jul. 15, 2014 or International Patent Application No. PCT/US2014/031237.

Bastin et al., "Salt Slection and Optimisation Procedures for Pharmaceutical New Chemical Entities", American Chemical Society and the Royal Society of Chemistry, vol. 4, No. 5, 2000, pp. 427-435.

Arnold, Instant Ketosis?, (2013), Aug. 4, 2013 (retrieved on Apr. 21, 2017), p. 1-3. Retrieved from the internet; URL: < http://patrickarnoldblog.com/instant-ketosis/. (Year: 2013).

Parker, Steve, "Ketogenic Mediterranean Diet: Version 2.3," Nov. 23, 2010, pp. 1-3. (Year: 2010).

Sajewicz et al. in Journal of Liquid Chromatography & Related Technologies, 33:1047-1057 (2010) (Year: 2010).

Shigeno etal. in Biosci. Biotech. Biochem., 56(2), 320-323 (1992) (Year: 1992).

Optical Purity and Enantiomeric Excess at https://www.masterorganicchemistry.com/2017/02/24/optical-purity-and-enantiomeric-excess/. (Retrieved from the Internet Nov. 6, 2018) (Year: 2018).

Tisdale, "Reduction of weight loss and tumour size in a cachexia model by a high fat diet", British Journal of Cancer, Jul. 1987, vol. 56, p. 39-43.

U.S. Appl. No. 14/455,385, filed Jan. 2, 2015, Office Action.
U.S. Appl. No. 14/860,092, filed Mar. 9, 2016, Office Action.
U.S. Appl. No. 14/860,092, filed Oct. 17, 2016, Office Action.
U.S. Appl. No. 15/610,668, filed Jul. 25, 2018, Office Action.
U.S. Appl. No. 15/454,157, filed Jan. 11, 2018, Office Action.
U.S. Appl. No. 15/454,157, filed Jun. 13, 2018, Office Action.
U.S. Appl. No. 15/936,820, filed Nov. 14, 2018, Office Action.
U.S. Appl. No. 15/936,849, filed Nov. 14, 2018, Office Action.
U.S. Appl. No. 15/936,849, filed Jan. 24, 2019, Notice of Allowance.

Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.

International Search Report cited in PCT/US19/27214 dated Jun. 25, 2019.

Written Opinion cited in PCT/US19/27214 dated Jun. 25, 2019.

U.S. Appl. No. 15/454,157, filed Feb. 26, 2019, Notice of Allowance.

U.S. Appl. No. 16,272,328, filed Jul. 29, 2019, Office Action.

COMPOSITIONS AND METHODS FOR DELIVERING CANNABIDIOL AND KETONE BODIES

CROSS-REFERENCE TO RELATED APPLICATIONS

This Application claims the benefit of and priority to U.S. Provisional Patent Application No. 62/769,412, filed Nov. 19, 2019, and to U.S. Provisional Patent Application No. 62/760,430, filed Nov. 13, 2018, and to U.S. Provisional Patent Application No. 62/723,274, filed Aug. 27, 2018, the disclosures of which are incorporated herein by reference in their entireties.

BACKGROUND

Ketosis

In periods of fasting, extreme exercise, and/or low carbohydrate consumption, glucose and glycogen stores in the body are rapidly used and can become quickly depleted. Failure to replenish glucose stores as they become depleted causes the body to metabolically shift to the creation of ketone bodies for energy. This metabolic state is called "ketosis".

Ketone bodies can be used by cells of the body as a fuel in addition or instead of glucose to satisfy the body's energy needs, including the brain and heart. During prolonged fasting, for example, blood ketone levels can increase to 2-3 mmol/L or more. It is conventionally understood that when blood ketones rise above 0.5 mmol/L, the heart, brain and peripheral tissues are using ketone bodies (e.g., beta-hydroxybutyrate and acetoacetate) as the primary fuel source. This condition is referred to as ketosis. Between 1.0 mmol/L and 3.0 mmol/L the condition is called "nutritional ketosis."

Upon transitioning into ketosis, or in other words, during ketogenic metabolism in the liver, the body uses dietary and bodily fats as a primary energy source. Consequently, once in ketosis, one can induce loss of body fat by controlling dietary fat intake and maintaining low carbohydrate intake to maintain a ketogenic metabolic state.

While in ketosis, the body is essentially burning fat for its primary fuel. The body initially cleaves fats into fatty acids and glycerol. It then transforms fatty acids into acetyl coenzyme A ("acetyl-CoA") molecules, which are then eventually transformed through ketogenesis into the water-soluble ketone bodies beta-hydroxybutyrate ("β-hydroxybutyrate" or "BHB"), acetoacetate, and acetone in the liver. BHB and acetoacetate are the ketone bodies used by the body for energy while acetone is removed as a by-product of ketogenesis. Although BHB is technically not a ketone, it is still referred to as a "ketone body" in the context of ketosis.

The metabolism of ketone bodies is associated with several beneficial effects. However, despite the many health advantages of pursuing a ketogenic diet or lifestyle and maintaining a state of nutritional ketosis, there remain significant barriers to pursuing and maintaining a ketogenic state. One of these barriers is the difficulty of transitioning into a ketogenic state. The fastest endogenous way to entering ketosis through depleting glucose stores in the body is through fasting combined with exercise. This is physically and emotionally demanding and is extremely challenging even for the most motivated and disciplined.

Additionally, the transition into ketosis is often accompanied by hypoglycemia which can cause lethargy and light-headedness in many, resulting in an uncomfortable physiological and mental state commonly referred to as the "low-carb flu" or "keto flu." In addition, many people experience a down regulation in their metabolism as the body goes into an "energy-saving" mode. Some suggest that these transitory symptoms may last as long as two to three weeks. During this transition period, if any meal or snack consisting of carbohydrates over the restrictive amount is consumed, there is a rapid termination of ketogenesis, causing the body to exit from its state of ketosis as the body shifts back to glucose utilization as its primary fuel. At this point, the difficult transition into ketosis must begin anew. Thus, despite the potential of a ketogenic diet for weight loss and other health benefits, serious limitations continue to hinder the full realization of its potential.

Cannabidiol

Cannabidiol (CBD) is one of the major cannabinoid constituents of the cannabis plant. Unlike tetrahydrocannabinol (THC), another major cannabinoid constituent of the cannabis plant, CBD does not have psychoactive effects. CBD is believed to have a counteractive effect on some of the negative effects of THC such as anxiety and disordered thinking. CBD is typically the second most abundant constituent of cannabis flowers/buds and the highest constituent of most other portions of the plant. It can account for up to 40% of the plant's extract.

CBD is currently used as an active ingredient in medicines intended to alleviate pain, particularly pain associated with multiple sclerosis, and in anti-seizure medicines intended to treat epilepsy. CBD is most commonly administered orally or via inhalation. CBD is believed to interact with a variety of biological targets, including cannabinoid receptors of the endocannabinoid system (ECS) and neurotransmitter receptors.

Though CBD has several positive uses and appears to be a promising drug agent, with other uses likely to be discovered in the future, some limitations to its use are currently known to exist. Use of CBD is associated with undesirable side effects such as light-headedness, general fatigue and malaise, and sleep disruption (see, e.g., Murillo-Rodriquez et al. "The nonpsychoactive Cannabis constituent cannabidiol is a wake-inducing agent" Behav. Neurosci. 2008 December, 122(6): 1378-82; and "Epidiolex" FDA Label, available at fda.gov). Thus, despite benefits associated with CBD as a supplement or drug, several limitations to its use remain.

BRIEF SUMMARY

Disclosed herein are compositions including a combination of: (1) cannabidiol (CBD) and/or cannabidiolic acid (CBDA); (2) a ketone body component such as beta-hydroxybutyrate (BHB) and/or acetoacetate; and (3) optionally a dietetically or pharmaceutically acceptable carrier. For ease of reference, such combination compositions may be referred to herein as "ketonnabidiol compositions" and "ketannabidiol compositions", which are each a portmanteau of "ketone" and "cannabidiol." Also disclosed herein are methods of using such ketonnabidiol compositions for producing desired physiological effects, such as fat loss, in a mammal.

In some embodiments, a ketonnabidiol composition may be utilized to beneficially enhance fat loss during ketosis while also reducing the duration and/or severity of unpleasant "keto flu" symptoms typically associated with ketosis. The ketone body component provides an exogenous source of ketone bodies for energy and can further induce and sustain a state of ketosis in the subject, while the CBD component functions to promote fat browning in the subject.

The fat browning effectively "primes" the subject for enhanced utilization of fat once ketone bodies are used as the primary energy source and more particularly while the subject is in a state of ketosis. This enables lipolysis and the metabolic utilization of lipids to more readily and/or more effectively occur. This can enable a faster transition into ketosis, more efficient utilization of fat during ketosis, and reduced duration and/or severity of hypoglycemic, keto flu effects during the transition into ketosis.

In addition, the ketonnabidiol compositions described herein enhance certain functions of the endocannabinoid system (ECS). The effects of CBD on the ECS in combination with the metabolic effects and/or molecular signaling effects of ketone bodies can promote a variety of beneficial physiological effects. For example, when the ECS is enhanced and the body is simultaneously utilizing ketone bodies as an energy source, one or more beneficial physiological effects can result. Examples include one or more of appetite suppression, neuroprotection, memory enhancement, anxiolytic effects, anti-depressant effects, anti-inflammation effects, antioxidant effects, analgesic effects, anti-aging/longevity, anti-tumorigenic effects, cardiovascular protection, and sleep promotion. These effects may be synergistically enhanced by the combined use of both the CBD component and the ketone body component. The ketone body component of the composition can also offset certain negative effects of CBD, such as sleepiness, light-headedness, general fatigue, malaise, and sleep problems.

Ketonnabidiol compositions described herein may be provided as a solid, powder, liquid, gel, or other dietetically or pharmaceutically acceptable form. The compositions can be administered as a dietary supplement mixed with food or drink, in the form of one or more capsules or tablets, or in liquid form such as a mouth spray or energy shot, for example.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

I. Definitions

The compound "cannabidiol" or "CBD" is one of the major cannabinoid constituents of the cannabis plant and is shown in Formula I (conformational isomers thereof may also be utilized):

Formula I

The term "ketone body" refers to compounds capable of being utilized by the body as an energy source and includes the compounds beta-hydroxybutyrate (BHB) and acetoacetate. Ketone body precursors may additionally or alternatively be utilized in the compositions described herein. Suitable ketone body precursors include, but are not limited to, 1,3-butanediol, medium chain fatty acids, and esters of medium chain fatty acids such as medium chain triglycerides. Ketone body compounds and ketone body precursor compounds are described in more detail below.

The compound "beta-hydroxybutyrate," also known as β-hydroxybutyrate, 3-hydroxybutyrate, βHB, or BHB, is the deprotonated form of beta-hydroxybutyric acid, which is a hydroxycarboxylic acid having the general formula $CH_3CH_2OHCH_2COOH$. The deprotonated form present at typical biological pH levels is $CH_3CH_2OHCH_2COO^-$. The general chemical structure of Formula II represents BHB compounds that may be utilized in the disclosed compositions (conformational isomers thereof may also be utilized):

Formula II where,
X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid with a strong or weak base, such as an alkali or alkaline earth metal hydroxide, carbonate, or bicarbonate, basic amino acid, and the like.

BHB may be utilized by a patient's body as an energy source during instances of low glucose levels in the subject or when a patient's body is supplemented with a usable form of BHB. Although not technically a "ketone", one of skill in the art will recognize that BHB, in the context of ketosis, is commonly referred to as a "ketone body."

BHB is a chiral compound and can exist as the R-enantiomer or the S-enantiomer, a racemic mixture, or a mixture where one of the enantiomers is enriched relative to the other. Endogenous BHB produced by the body is the R-enantiomer and therefore the form that is more readily available as a ketone body. BHB can be transformed by the body into acetoacetate, which is not chiral, and acetoacetate can be transformed by the body into the R-enantiomer. It is believed that the S-enantiomer of BHB can be transformed into the R-enantiomer by first being converted into acetoacetate and then into the R-enantiomer.

The compound "acetoacetate" is the deprotonated form of acetoacetic acid, which is a carboxylic acid having the formula $CH_3COCH_2COOH$. The deprotonated form present at typical biological pH levels is therefore $CH_3COCH_2COO^-$. As stated above, the body can transform BHB into acetoacetate and vice versa. As with BHB, acetoacetate may be utilized as an energy source during ketosis. The general chemical structure of Formula III represents acetoacetate compounds that may be utilized in the disclosed compositions (conformational isomers thereof may also be utilized):

Formula III where,
X can be hydrogen, metal ion, amino cation, such as from an amino acid, alkyl, alkenyl, aryl, or acyl.

As with BHB, acetoacetate may be utilized by a patient's body as an energy source during instances of low glucose levels in the subject or when a patient's body is supplemented with a usable form of acetoacetate. Unlike BHB, acetoacetate is a true "ketone", and in the context of ketosis is commonly referred to as a "ketone body" along with BHB.

BHB and acetoacetate compounds are preferably provided in salt and/or ester form, although they can also be administered in acid form, or as a mixture of salt, ester and/or acid forms. Exemplary salt forms include sodium, potassium, calcium, magnesium salts, and lithium. Some embodiments include one or more transition metal salts. Transition metal cations suitable for use as part of a salt include chromium, manganese, cobalt, copper, zinc, iron, (e.g., as an iron II or iron III cation), molybdenum, and selenium. Other suitable salt forms include cations of organic compounds capable of having a net positive charge, including amino acids or their derivatives/metabolites such as arginine, lysine, leucine, iso-leucine, histidine, ornithine, creatine, agmatine, L-glutamine, and citrulline.

L-arginine is also known to promote formation of nitric oxide (NO) in the blood, which can help heart patients and men with erectile dysfunction. Other natural substances that can boost blood NO levels and improve erection quality include beets, citrus (orange, lemon, grapefruit), pomegranate, dark chocolate, walnuts, arugula, spinach, watermelon, meat, seafood, garlic, cordyceps, maca root, panax ginseng, eleuthero root, rhodiola rosea, moringa leaf, yerba mate, goosefoot, safed musli, desmodium, spirulina, pycnogenol, hawthorn extract, icariin, grape seed extract, vitamin D, L-citrulline, and horny goat weed. PDE5 inhibitors can also be used to treat heart patients and erectile dysfunction. Examples include avanafil, lodenafil, mirodenafil, sildenafil, tadalafil, vardenafil, udenafil, zaprinast, icariin, benzamidenafil, and dasantafil.

Suitable ester forms of BHB include mono-esters of ethanol, mono-esters of 1-propanol, mono-esters of 1,3-propanediol, di-esters of 1,3-propanediol, mono-esters of 5-1,3-butanediol, mono-esters of R-1,3-butanediol, di-esters of 1,3-butanediol, mono-esters of glycerin, di-esters of glycerin, and tri-esters of glycerin. 1,3-butanediol is a metabolic BHB precursor that may be additionally or alternatively be utilized as a source of BHB and/or acetoacetate compounds. The acid forms of BHB and acetoacetate typically have an unpleasant taste but can be used by appropriate taste masking mechanisms, such as one or more capsules, tablets, or other bolus.

The beta-hydroxybutyrate and acetoacetate compositions may be provided in three general forms: 1) a salt form, 2) an ester form, and 3) a free acid form (i.e., beta-hydroxybutyric acid and acetoacetic acid). The compositions described herein may be provided in any one of these forms or as a mixture combining at least two of these forms.

Each of the different forms has its own properties and its own potential benefits and limitations. For example, ester forms of beta-hydroxybutyrate typically have poor organoleptic properties relative to the other forms of beta-hydroxybutyrate. That is, ester forms of beta-hydroxybutyrate are often described as having a pungent taste and/or smell.

Salt forms of beta-hydroxybutyrate are generally considered to taste better than ester forms. However, administration of clinically or dietetically effective doses of beta-hydroxybutyrate and/or acetoacetate in salt form inherently requires administration of relatively high levels of the corresponding cations. Sodium, for example, is often used as the cation in beta-hydroxybutyrate salts, and high levels of sodium have well-known negative health effects. Although different salts having different cations may be mixed to dilute the impact of a single cation, it can still be difficult to provide effective amounts of ketone bodies without upsetting the electrolyte balance in the subject/patient.

The free acid form of beta-hydroxybutyrate (i.e., beta-hydroxybutyric acid) and/or acetoacetate (i.e., acetoacetic acid) may also be utilized. However, because of the relatively low pKa values (e.g., beta-hydroxybutyric acid has a pKa of 4.70), these compounds deprotonate and produces $H^+$ at physiological pH. The resulting excess acidity can cause undesirable side effects including causing or aggravating gastrointestinal issues such as ulcers or reflux.

Combining different forms of beta-hydroxybutyrate can beneficially limit the occurrence and/or severity of these undesirable side-effects and/or can permit administration of higher doses of ketone bodies. For example, a combined form can deliver the same amount of ketone bodies as a single form without causing the same occurrence and/or severity of side-effects. Likewise, a combined form can deliver a greater amount of ketone bodies than a single form before reaching similar occurrence and/or severity of side-effects.

In other words, for a given dose of beta-hydroxybutyrate and/or acetoacetate, a combined form, and in particular the triple form, is expected to have less 1) organoleptic side-effects, 2) electrolyte imbalance side-effects, and/or 3) acidity side-effects as compared to the single form. For example, a single form ester may have a threshold dosage that the typical user will not exceed because of the negative organoleptic side-effects, a single form salt may have a threshold dosage limited by the recommended dietary limits of the electrolytes administered with the salt, and a single form acid may have a threshold dosage that the typical user will not exceed because of the negative effects of acidity. The combined forms, and in particular the triple form, may allow supplementation of greater amounts of ketone bodies with- out exceeding any of the thresholds related to organoleptic, electrolyte, or acidity side-effects.

In some embodiments, a triple form ketone body component includes at least about 2% of the ester form, at least about 2% of the salt form, and at least about 2% of the free acid form on a molar basis of beta-hydroxybutyrate and/or acetoacetate. In other words, at least about 2% of the number of ketone body molecules (beta-hydroxybutyrate and/or acetoacetate) are provided by each separate form. More preferably, a triple form includes at least about 5% ester form, at least about 5% salt form, and at least about 5% free acid form on a molar basis of ketone bodies, or at least about 10% ester form, at least about 10% salt form, and at least about 10% free acid form on a molar basis of ketone bodies, or at least about 20% ester form, at least about 20% salt form, and at least about 20% free acid form on a molar basis of ketone bodies, or at least about 30% ester form, at least about 30% salt form, or at least about 30% free acid form on a molar basis of ketone bodies.

In some embodiments, a triple form ketone body component includes an ester form at about 2% to about 96%, or about 5% to about 90%, or about 10% to about 80%, or about 20% to about 60% on a molar basis of ketone bodies, includes a salt form at about 2% to about 96%, or about 5% to about 90%, or about 10% to about 80%, or about 20% to about 60% on a molar basis of ketone bodies, and includes an acid form at about 2% to about 96%, or about 5% to about 90%, or about 10% to about 80%, or about 20% to about 60% on a molar basis of ketone bodies.

It is also possible to form an ester between BHB and CBD, in which the carboxyl group of a BHB molecule is esterified with one (monoester form) or both (diester form) hydroxyl groups of a CBD molecule. Such ester forms of BHB and CBD can be used to provide a stabilized compound with specific ratios of BHB and CBD. Depending on whether one or both hydroxyl groups of CBD is/are esterified with BHB, and depending on the ratio of monoester to diester forms included in the composition, the ratio of BHB to CBD may be in a range of about 1:1 to about 2:1. The ester can also be enriched with additional BHB and/or CBD molecules (e.g., free or salt forms or other ester forms) to readily provide other desired ratios of BHB to CBD. Formula IV represents an exemplary BHB and CBD ester where both OH groups of the CBD have been esterified (conformational isomers thereof may also be utilized).

Formula IV

Similarly, it is possible to form an ester between acetoacetate and CBD, in which the carboxyl group of an acetoacetate molecule is esterified with one or both hydroxyl groups of a CBD molecule. Such ester forms of acetoacetate and CBD can be used to provide a stabilized compound with specific ratios of acetoacetate and CBD. Depending on whether one or both hydroxyl groups of CBD is/are esterified with acetoacetate, the ratio of acetoacetate to CBD may be in a range of about 1:1 to about 2:1. The ester can also be enriched with additional acetoacetate and/or CBD molecules (e.g., free or salt forms or other ester forms) to provide other ratios of acetoacetate to CBD. Formula V represents an exemplary acetoacetate and CBD ester where both OH groups of the CBD have been esterified (conformational isomers thereof may also be utilized).

Formula V

Some embodiments may include a CBD diester where each ester bond is formed with a different ketone body. For example, a CBD molecule may form one ester bond with a BHB group (such as one of the ester bonds of Formula IV) and another ester bond with an acetoacetate group (such as one of the ester bonds shown of Formula V).

Providing the compound in an ester form may beneficially enhance the solubility and/or bioavailability of the compound. For example, the esterified forms of CBD as described herein may have reduced hydrophobicity relative to non-esterified CBD. Such esters may be formed using known esterification techniques such as, for example, Fischer esterification.

The BHB compound can be provided as a racemic mixture of enantiomers, sometimes referred to DL-beta-hydroxybutyrate (alternatively RS-beta-hydroxybutyrate), which can be made synthetically. In humans, the enantiomer D-3-hydroxybutyrate ("D-beta-hydroxybutyrate", "D-BHB", "R-hydroxybutyrate" or "R-BHB") is synthesized in the liver from acetoacetate, the first ketone produced when in a state of ketosis. Therefore, it may be desirable to provide BHB as the enantiomer D-3-hydroxybutyrate to increase potency, either enriched relative to L-3-hydroxybutyrate ("L-beta-hydrobutyrate", "L-BHB", "S-beta-hydrobutyrate" or "5-BHB") or isolated from L-3-hydroxybutyrate. Alternatively, it may be desirable to provide BHB as the enantiomer L-3-hydroxybutyrate to increase potency, either enriched relative to D-3-hydroxybutyrate or isolated from D-3-hydroxybutyrate. Administering D-3-hydroxybutyrate, the endogenous form, results in attaining rapid elevated ketosis, while administering L-3-hydroxybutyrate, which must first be converted D-3-hydroxybutyrate, may provide slower and more sustained ketosis. D-3-hydroxybutyrate is also referred to as "R-beta-hydroxybutyrate" and L-3-hydroxybutyrate is also referred to as "S-beta-hydroxybutyrate."

As used herein, a "ketonnabidiol composition" refers to a combination composition that includes: (1) cannabidiol (CBD) and/or cannabidiolic acid (CBDA); (2) a ketone body component such as beta-hydroxybutyrate (BHB) and/or acetoacetate; and (3) optionally a dietetically or pharmaceutically acceptable carrier. CBDA is the metabolic precursor of CBD within the cannabis plant and is structurally and functionally similar to CBD. CBDA includes an additional carboxyl group that is believed to readily undergo decarboxylation in physiological conditions to produce CBD. Though the examples provided herein will typically refer only to CBD, it will be understood that direct precursor compounds such as CBDA may additionally or alternatively be used as the respective component of the ketonnabidiol composition.

As used herein, "subject," "patient," or "user" refers to mammals, including humans and other primates. The subject may be any mammal requiring metabolic therapy, treatment, or prophylaxis, or any mammal suspected of requiring metabolic therapy, treatment, or prophylaxis. Prophylaxis means that regiment is undertaken to prevent a possible occurrence, such as where a high risk of diabetes or other metabolic disorder is identified. "Patient," "subject," and "user" are used interchangeably herein.

"Ketosis" as used herein refers to a subject having blood ketone levels within the range of about 0.5 mmol/L to about 16 mmol/L. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis," or it denotes an altered metabolism in which fat becomes the predominant energy source, consequently shifting the body from a state of fat storage to a state of fat oxidation.

The term "administration" or "administering" is used herein to describe the process in which the ketogenic compositions are delivered to a subject. The composition may be administered in various ways including oral, intragastric, nasal or pulmonary, as an injectable (e.g., subdermal, parenteral, or intravenous), as a suppository, etcetera.

The term "unit dose" refers to a dosage form that is configured to deliver a specified quantity or dose of composition or component thereof. Example dosage forms include, but are not limited to, tablets, capsules, powders, food products, food additives, beverages (such as flavored, vitamin fortified, or non-alcoholic), beverage additives (such as flavored, vitamin fortified, or non-alcoholic), candies, suckers, pastilles, food supplements, dietetically acceptable sprays (such as flavored mouth spray), injectables (such as an alcohol-free injectable), and suppositories. Such dosage forms may be configured to provide a full unit dose or fraction thereof (e.g., ½, ⅓, or ¼ of a unit dose).

Another dosage form that can be used to provide a unit dose of composition or component thereof is a unit dose measuring device, such as a cup, scoop, syringe, dropper, spoon, or colonic irrigation device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as spoons, spatulas, cups, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

II. Ketonnabidiol Compositions

Ketonnabidiol compositions described herein may comprise: (1) cannabidiol (CBD) and/or cannabidiolic acid (CBDA); (2) a ketone body component such as beta-hydroxybutyrate (BHB) and/or acetoacetate; and (3) optionally a dietetically or pharmaceutically acceptable carrier.

Some ketonnabidiol compositions may include one or more other cannabinoids in addition to or as an alternative to CBD. For example, some embodiments may include amounts of THC, tetrahydrocannabivarin (THCV), cannabigeriol (CBG), cannabidivarin (CBDV), cannabichromene (CBC), cannabinol (CBN), cannabielsoin (CBE), iso-THC, cannabicyclol (CBL), cannabicitran (CBT), cannabivarin (CBV), cannabichromevarin (CBCV), cannabigerovarin (CBGV), cannabigerol monomethyl ether (CBGM), other cannabis-derived cannabinoids, a carboxylic acid form thereof, and combinations thereof. Some embodiments may intentionally omit one or more non-CBD cannabinoids such as THC to reduce or eliminate intoxication.

For example, THCV can be used to assist with weight loss, treat symptoms associated with diabetes, assist with treating anxiety and post-traumatic stress disorder (PTSD), and treat neuro-disorders. CBG can be used to treat pain and inflammation, increase anti-oxidant levels, help skin disorders (psoriasis/acne), is anti-fungal, and helps with neuro-disorders. CBC can be used to block pain and inflammation, provide synergy with other cannabinoids (entourage effect), and promote anandamide (the bliss molecule). CBN can be used as a powerful sedative, to help increase appetite, help treat psoriasis, as an analgesic, and as an anti-convulsant and anti-emetic.

Ketonnabidiol compositions described herein may also include one or more additional non-cannabinoid terpenes and/or terpenoids in addition to the cannabinoid component. For example, certain compositions may include one or more terpenes and/or terpenoids associated with the cannabis plant, such as alpha-pinene, myrcene, limonene, caryophyllene, linalool, humulene, ocimene, and terpinolene. Such terpenes and/or terpenoids may be utilized along with the cannabinoid component to modulate bioavailability and/or neuroavailability of the cannabinoid component via the entourage effect.

Although most of the ketonnabidiol examples described herein utilize CBD, some embodiments may substitute one or more related cannabinoids, including one or more of those described above, as an alternative to the CBD component. In particular, some embodiments may include one or more cannabinoids that are structurally and/or functionally related to CBD, such as those that are cyclized from a precursor compound (e.g., CBG or CBGV) in a way that maintains both hydroxyl groups.

Just as the CBD may be provided as a monoester or diester form where the CBD molecule is bonded with one or two ketone body moieties (e.g., a BHB and/or acetoacetate group), other cannabinoids included in the composition may also be provided in an ester form that combines the cannabinoid molecule with one or more ketone body moieties via an ester bond, such as by bonding the carboxyl group(s) of one or more ketone bodies to one or more available hydroxyl groups of the cannabinoid. For example, some embodiments may include THC in addition to CBD. The THC may be provided as an ester by bonding the carboxyl group of a ketone body (e.g., BHB or acetoacetate) with the single hydroxyl group of THC.

A ketonnabidiol composition may also optionally include a supplemental source of ketone body precursors such as one or more of 1,3-butanediol, fatty acids, and/or esters of fatty acids. A typical ester form of fatty acids is a mono-, di-, or triglyceride. Preferred forms of fatty acids and their esters are medium chain fatty acids and medium chain triglycerides (MCT), though short and/or long chain fatty acids and their esters may also be utilized. In embodiments where used, a medium chain fatty acid has from 6 to 12 carbons, preferably from 8 to 10 carbons. Compositions and methods related to the combination of BHB with a medium chain fatty acid, or ester thereof, are disclosed in U.S. Pat. No. 9,138,420, which patent is incorporated herein by this reference in its entirety. Such compounds may be utilized as the ketone body component of the ketonnabidiol compounds described herein.

Exemplary fatty acids are caprylic acid, also known as octanoic acid, comprising 8 carbon molecules, and capric acid, also known as decanoic acid, comprising 10 carbon molecules. Because MCTs are ketone body precursors, including one or more MCTs may provide an additional source for the production of ketone bodies independent of the BHB and acetoacetate compounds, thus helping to promote sustained elevation of ketone levels to a desired therapeutic level. The term "short chain triglycerides" (SCT) refers to molecules similar to MCT molecules but with short chain fatty acids (6 carbon atoms or less in length) attached to the glycerol backbone. The term "long chain triglycerides" (LCT) refers to molecules similar to MCT molecules but with long chain fatty acids (12 carbon atoms or more in length) attached to the glycerol backbone.

Examples and sources of the medium chain fatty acid, or an ester thereof such as a medium chain triglyceride, include coconut oil, coconut milk powder, fractionated coconut oil, palm oil, palm kernel oil, caprilic acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc.

When medium chain fatty acids, fatty acid esters, or mono-, di- or triglycerides of medium chain fatty acids are provided, the composition is preferably administered such that the weight ratio of ketone bodies to medium chain fatty acid (or ester thereof) ranges from about 4:1 to about 1:4, or from about 2:1 to about 1:2, or from about 1.5:1 to about 1:1.5. The same ratios may be used when short chain fatty acids (or esters thereof) or long chain fatty acids (or esters thereof) are additionally or alternatively used.

In alternative embodiments, the compositions may further include one or more short and/or long chain fatty acids, fatty acid esters, or mono-, di- or triglycerides of short and/or long chain fatty acids in order to provide an additional source of ketone bodies for sustaining ketosis. In some embodiments, the composition is preferably administered such that the ratio of BHB/acetoacetate to medium, short and/or long chain fatty acid (or ester thereof) ranges from about 4:1 to about 1:4, or from about 2:1 to about 1:2, or from about 1.5:1 to about 1:1.5.

Examples of short chain fatty acids include acetic acid, propionic acid, butyric acid, isobutyric acid, valeric acid, isovaleric acid, and caproic acid. Examples of medium chain fatty acids include caprylic acid, capric acid, and lauric acid. Examples of long-chain fatty acids include lauric acid, myristic acid, palmitic acid, stearic acid, arachidic acid, behenic acid, lignoceric acid, cerotic acid, omega-3 fatty acids, omega-6 fatty acids, omega-7 fatty acids, and omega-9 fatty acids.

As described above, ketonnabidiol compositions may be formulated with various ratios of ketone body component to CBD. Ketonnabidiol compositions may also be formulated with various ratios of different forms of ketone bodies to one another. That is, some embodiments may include a greater proportion of BHB relative to acetoacetate, whereas other embodiments may include a greater proportion of acetoacetate relative to BHB. For example, the BHB to acetoacetate ratio may be about 0.1:1, 0.25:1, 0.5:1, 0.75:1, 1:1, 1.25:1, 1.5:1, 2:1, 4:1, 9:1, or may be within a range having any two of the foregoing ratios as endpoints. The ratio may be formulated according to particular application needs and preferences. For example, BHB-based ketonnabidiol compositions are believed to have greater relative effect on metabolic activity (e.g., fat loss, anti-inflammation, vasodilation) while acetoacetate-based ketonnabidiol compositions are believed to have greater relative effect on neurological activity (e.g., neuroprotection, anxiolytic and anti-depressant effects, memory).

Thus, where the primary intended effects are metabolic in nature, a ketonnabidiol composition may be formulated so that BHB makes up at least about 50%, or at least about 75%, or at least about 95%, or even about 100% of the content of the ketone body component. On the other hand, where the primary intended effects are neurological in nature, a ketonnabidiol composition may be formulated so that acetoacetate makes up at least about 50%, or at least about 75%, or at least about 95%, or even about 100% of the content of the ketone body component.

III. Treatment Effects

The administration of a ketonnabidiol composition may provide a variety of beneficial physiological effects, including one or more of fat loss, appetite suppression, antioxidant effects, neuroprotection, memory enhancement, anxiety mediation, suppression of depressive symptoms, analgesic effects, anti-inflammatory effects, cardiovascular benefits (e.g., vasodilation and blood pressure modulation), anti-aging/longevity, anti-tumorigenic effects, and sleep enhancement, for example.

Though a variety of different pharmacological and/or physiological variables may be involved, the combination compositions described herein may enable complementary enhancement of several different physiological systems. Without being bound to any particular theory, it is presently believed that the CBD component functions to enhance the subject's endocannabinoid system (ECS) while the exogenous ketone body component functions to further modulate and/or complement the effects on the ECS via metabolic activity and/or molecular signaling activity, resulting in synergistically enhanced effects not capable with either component independently.

For example, CBD's pharmacological activity appears to relate in part to its inhibition of the enzyme fatty acid amide hydrolase (FAAH) (see, e.g., Campos et al., "Multiple mechanisms involved in the large-spectrum therapeutic potential of cannabidiol in psychiatric disorders," *Philosophical Transactions of the Royal Society of London*, 367 (1607): 3364-78). The FAAH enzyme is responsible for the breakdown of endocannabinoids such as anandamide. CBD may therefore function as an endocannabinoid reuptake and breakdown inhibitor, thereby sustaining higher levels of endocannabinoids in the subject's tissues, including in the brain's synapses (see, e.g., Deutsch, "A Personal Retrospective: Elevating Anandamide (AEA) by Targeting Fatty Acid Amide Hydrolase (FAAH) and the Fatty Acid Binding Proteins (FABPs)," Front. Pharmacol. 2016 Oct. 13; 7:370).

The ECS is involved in many physiological functions and has been shown to have a homeostatic role in regulating metabolic functions such as energy storage and nutrient transport. The additional use of exogenous ketone bodies enables the subject to simultaneously benefit from the body's use of the ketone bodies as a metabolic energy source and/or from the molecular signaling activity of the ketone bodies. As an example of beneficial molecular signaling, BHB may affect histone proteins, altering gene expression in beneficial ways such as by promoting expression of mitochondria enzymes related to oxidative phosphorylation and the electron transport chain, PPARα (a protein with the ability to speed up the breakdown of fat), and the like. BHB may also upregulate expression of mitochondrial regulator proteins such as peroxisome proliferator-activated receptor gamma coactivator 1-alpha (PGC-1α), sirtuin 3, and mitochondrial uncoupling protein 2 (UCP2) (see Hasan-Olive et al. "A Ketogenic Diet Improves Mitochondrial Biogenesis and Bioenergetics via PGC1a-SIRT3-UCP2 Axis" Neurochem. Res. (2018)). BHB may also stimulate chaperone-mediated autophagy of certain proteins marked by BHB oxidative modification (see Finn et al. "Ketone bodies stimulate chaperone-mediated autophagy" J. Biol. Chem. 2005 Jul. 8; 280(27): 25864-70). Acetoacetate may have molecular signaling functions similar to those of BHB, as they are treated similarly in the body and since the body can readily convert between the two compounds.

In addition to the benefits associated directly with exogenous ketone body supplementation, the ketone body component can also function to effectively put the subject in a state of active ketosis. Ketone body supplementation effectively "primes" the subject for more metabolically efficient transport and utilization of consumed lipids, and this effect is further bolstered when the subject is in an active state of ketosis. CBD, as a lipid itself, is therefore believed to have enhanced pharmacokinetics (e.g., more effective absorption, transport, cell permeation, etc.) when the subject is actively utilizing ketone bodies as an energy source, particularly when the subject is in a state of ketosis as opposed to a regular state of (primarily) glycolysis. For example, administration of CBD to a subject in combination with exogenous ketone bodies, where preferably the subject is also in a state of elevated and/or sustained ketosis as a result of supplementation with the ketone bodies, may result in about 10%, 20%, 40%, or 75% or more higher utilization of the CBD as compared to CBD supplementation without a ketone body component.

One of the overall effects of ketonnabidiol supplementation is improved homeostasis, which can have a wide-ranging influence on a variety of other physiological systems, as explained in more detail below. The ECS has far reaching activity and functions to promote homeostasis throughout several physiological systems. The immune system also regulates essentially all of the body's tissues to assist in maintaining equilibrium in the face of frequent stresses such as pathogens, antigens, pollution, and poor diet. The components of a ketonnabidiol composition beneficially function to enhance the homeostasis/equilibrium promoting activities of the ECS and the immune system.

The following beneficial treatment effects may be achieved or enhanced as a result of supplementation with a ketonnabidiol composition. Although many of the examples are described in the context of a subject being in a state of ketosis, it will be understood that realization of the beneficial effects does not necessarily require the subject to be in a state of ketosis. In other words, beneficial effects may be realized as a result of co-administration of the exogenous ketone body component and the CBD. These effects may be further enhanced once the subject enters an active state of ketosis, and the exogenous ketone body component can itself aid in getting the subject into such a state, but ketosis is not necessarily a requirement for realizing these effects.

A. Fat Loss

Figure 1:
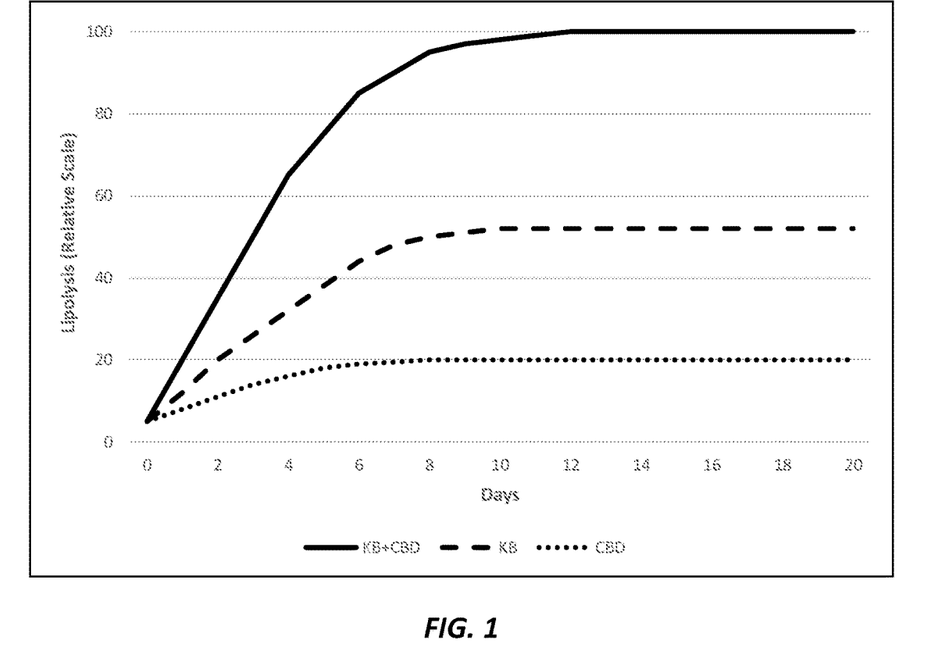
FIG. 1 schematically illustrates expected relative rates of lipolysis resulting from different respective treatments of CBD only, BHB only, and a combination of BHB and CBD, showing that the rate of lipolysis is higher with the combination treatment by more than the sum of the BHB only and CBD only treatments.

FIG. 1 schematically illustrates expected relative rates of lipolysis resulting from different respective treatments of CBD only (CBD), the ketone body BHB only (KB), and a combination of the same amounts of BHB and CBD (KB+CBD), showing that the rate of lipolysis is higher with the combined (i.e., ketonnabidiol) treatment by more than the sum of the BHB only and CBD only treatments. The ketonnabidiol treatment is expected to more quickly induce higher rates of lipolysis in addition to leading to overall higher rates of lipolysis.

Without being bound to any particular theory, it is believed that the different components of the ketonnabidiol composition provide synergistic effects that aid in promoting lipolysis and fat loss when administered together. CBD is believed to induce fat browning (see, e.g., Parray and Yun, "Cannabidiol promotes browning in 3T3-L1 adipocytes" Mol. Cell Biochem., 2016 May; 416 (1-2): 131-9). That is, CBD functions to convert some of what is usually white adipose tissue ("white fat") to brown adipose tissue ("brown fat"). As compared to white fat, brown fat is more metabolically active, includes more mitochondria, and is much more readily broken down and used by the body for energy. Higher levels of brown fat are associated with greater stimulation of genes and proteins that enhance the oxidation of fat, increases in the number and activity of mitochondria, and decreases in the expression of proteins involved in lipogenesis. The ratio of brown fat to white fat is also known to fall with age, so increasing brown fat may be particularly useful for relatively older subjects.

The CBD component of the ketonnabidiol composition therefore promotes the conversion of white fat into brown fat. At the same time, the ketone body component of the ketonnabidiol composition promotes the induction of ketosis and metabolically shifts the body toward the breakdown of fat to make additional ketone bodies. The higher levels of brown fat resulting from the CBD more readily allow for fat breakdown and lipolysis as the subject utilizes ketone bodies for energy and preferably also enters ketosis. In other words, with higher levels of brown fat, the subject is able to more readily enter ketosis and begin breaking down fat as a source of ketone bodies for energy. In addition, the increased availability of ketone body precursors (e.g., lipids) resulting from the increased levels of lipolysis can accelerate the production of endogenous ketones in the liver.

The transition from a state of primarily glycolysis to a state of ketosis involves a metabolic shift as the subject ramps up the enzymes and other metabolic machinery necessary to utilize stored body fat as its primary source of energy. Higher levels of brown fat lessen the difficulty of this transition. Because brown fat is already more metabolically active than white fat, it is more readily utilized by the body as it transitions into ketosis. This means that the shift into ketosis may be relatively smoother and/or more rapid. White, visceral fat, on the other hand, has less vascularization and is less accessible by the body. It typically takes more time, with more associated unpleasant symptoms, to get to a state where such fat is being actively broken down as a primary fuel source.

As described above, the transition from a metabolic state where glucose is the primary fuel source to one in which ketone bodies are the primary fuel source, is often associated with uncomfortable symptoms related to hypoglycemia and the body's entry into an energy-saving mode. These symptoms lessen over time as the body becomes more efficient at utilizing fat to generate ketone bodies and at using the generated ketone bodies as its primary fuel source. Supplementation of exogenous ketone bodies such as BHB can promote the transition to ketosis by ensuring a sufficient and steady supply of ketone bodies, but by itself such supplementation does not increase the metabolic efficiency of using fat and ketone bodies.

Figure 2:
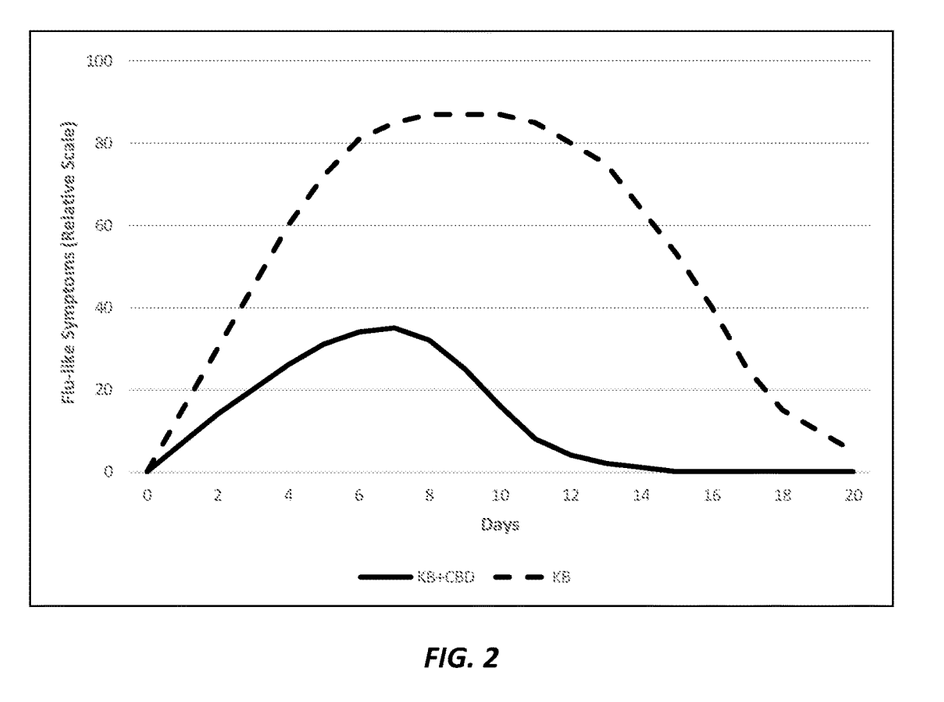
FIG. 2 illustrates expected relative levels of "keto flu" symptoms resulting from different respective treatments of BHB only and a combination of BHB and CBD, showing reduced severity and duration of symptoms with the combination treatment.

FIG. 2 schematically illustrates expected relative levels of "keto flu" symptoms resulting from different respective treatments of the ketone body BHB only (KB) and a combination of the same amounts of BHB and CBD (KB+CBD), showing reduced severity and duration of symptoms with the combination treatment. When entering ketosis, difficulties often arise when glucose stores are depleted but the body has not yet ramped up to comfortable levels of ketone body production. The uncomfortable symptoms are associated with the body entering a less active, energy-saving mode until efficiency in generating and using ketone bodies becomes sufficient.

It is believed that by combining CBD with exogenous ketone body supplementation, the increases in more metabolically active brown fat lead to a smoother transition from glucose utilization to ketone body production and utilization. In other words, because the body is able to more readily access, break down, and use stores of brown fat, the need for the body to enter into an energy saving state is minimized and the typical "keto flu" period is correspondingly reduced. The use of exogenous ketone bodies as an energy source during this initial period, in addition to the metabolic priming accomplished by the fat browning of the CBD, may therefore beneficially reduce the discomfort that prevents many from achieving the health benefits associated with ketosis.

This result is surprising and unexpected, particularly given the conventional association of CBD with side effects such as fatigue, light-headedness, and general malaise. The normal expectation is that such side effects would compound and aggravate the similar keto flu symptoms, yet the fat browning and lipolysis enhancing effects of CBD instead function to shorten the keto flu transition period and reduce the severity and/or duration of unpleasant symptoms. Further, the energy provided by ketone bodies during ketosis, which is induced and sustained by way of the supplemented exogenous ketones, can counteract remaining side effects associated with the CBD.

CBD is also believed to be a negative allosteric modulator of the cannabinoid receptor $CB_1$. That is, CBD is believed to interact with the $CB_1$ receptor and changes the shape of the receptor in a way that weakens its ability to bind to other ligands. In the liver, activation of the $CB_1$ receptor is known to increase lipogenesis (see, e.g., Osei-Hyiaman et al. "Endocannabinoid activation at hepatic $CB_1$ receptors stimulates fatty acid synthesis and contributes to diet-induced obesity" J. Clin. Invest. 115 (5): 1298-305). CBD may therefore limit the generation of new fat, and this additional effect of CBD further assists the fat loss function of the ketonnabidiol compositions. In addition, by limiting the generation of new fat, a higher proportion of consumed fat will be available for use as an energy source in ketosis, limiting keto flu symptoms.

B. Appetite Suppression

The endocannabinoid system plays a major role in appetite regulation. THC is infamously known for causing an increased appetite, and this is believed to be due at least in part to its activation of $CB_1$ receptors in the hypothalamus. CBD, however, appears to have the opposite effect, which may be due in part to CBD's activity as a negative allosteric modulator of $CB_1$ receptors.

Exogenous ketone bodies are also associated with appetite suppression, and can provide a readily available fuel source for the body and the brain with rapid effects on satiety. In addition, $CB_1$ receptors are associated with release of ghrelin, the "hunger hormone." Exogenous ketone body supplementation can lower ghrelin levels, thereby suppressing appetite and perceived hunger. Further, when in a state of ketosis, energy levels are more balanced and regular as opposed to the highs and lows associated with a diet higher in carbohydrates. Cravings that often occur during these energy lows (e.g., "sugar crashes") are reduced or eliminated with exogenous ketone body supplementation and during ketosis.

It is expected that the appetite suppressing effects of CBD and ketone bodies are synergistically enhanced as a result of their combined administration. The ketone body component of the composition is expected to reduce appetite and to aid in inducing and sustaining ketosis in the subject, which will further lead to reduced appetite. Further, the CBD component is expected to further reduce appetite through its modulation of the endocannabinoid system. It is expected that the resulting appetite suppression effects will be greater than that possible with either component alone and/or will be greater than the sum of the effects of each component when used independently.

C. Neuroprotection/Memory

The endocannabinoid system also plays a major role in memory processing. THC is known to have a memory impairment effect. CBD, on the other hand, appears to enhance memory. CBD is also a potent antioxidant and has an associated neuroprotective effect, a fact that is utilized in the formation of CBD containing anti-seizure drugs. CBD may also provide neuroprotective effects by inhibiting the reuptake and breakdown of anandamide, an endocannabinoid, in the synapses of the brain.

Neuroprotection and enhanced memory are also effects associated with exogenous ketone body supplementation as well as with ketosis, which may be induced by the use of exogenous ketone bodies. When the brain switches from using glucose as its primary fuel source to using ketone bodies as its primary fuel source, the resulting metabolic state provides additional protection against neurodegenerative conditions such as epilepsy and possibly Alzheimer's and Parkinson's diseases (see, e.g., Gasior et al. "Neuroprotective and disease-modifying effects of the ketogenic diet" Behay. Pharmacol. 2006 September; 17 (5-6): 431-39).

Ketone bodies, in particular BHB, are potent free radical scavengers and provide direct antioxidant effects. Because the brain actively utilizes ketone bodies when they are available, the relatively high concentration of ketone bodies in the brain following supplementation therefore provides an effective antioxidant neuroprotective function. Further, BHB molecular signaling provides indirect antioxidant effects via endogenous enzyme upregulation. For example, BHB molecular signaling may be associated with Class I and II histone deacetylase (HDAC) inhibition, which is related to mitigation of neurodegenerative diseases (e.g., Alzheimer's disease and Huntington's disease), and has positive effects on memory, among other effects. BHB may also increase gene expression of various endogenous defense proteins such as FOXO3 (tumor inhibitor), reactive oxygen species (ROS) scavengers such as catalase and SOD2, and toxic metal scavengers such as metallothionein. BHB may also act as an agonist of the $HCA_2$ protein. As with high-dose niacin supplementation, this is associated with anti-inflammatory effects in a variety of tissues including the brain.

It is expected that the neuroprotective and/or memory enhancing effects of CBD and ketone bodies are synergistically enhanced as a result of their combined administration. The ketone body component of the composition is expected to provide these effects and also to aid in inducing and sustaining ketosis in the subject, which will lead to neuroprotective and/or memory enhancing effects. Further, the CBD component is expected to further provide neuroprotection and/or memory enhancement through its modulation of the endocannabinoid system. It is expected that the resulting neuroprotective and/or memory effects will be greater than that possible with either component alone and/or will be greater than the sum of the effects of each component when used independently. The beneficial neuroprotective effects of a ketonnabidiol composition may be particularly useful in treating and/or managing Alzheimer's disease, Parkinson's disease, and epilepsy, for example.

D. Anti Aging/Longevity

The ability of CBD to enhance the ECS can promote longevity in the user. Disruptions in the ECS can increase with age, and the ECS may therefore be a suitable therapeutic target for age-related conditions (see, e.g., Paradisi et al. "The Endocannabinoid System in Ageing: A New Target for Drug Development" Current Drug Targets 2006, 7). CBD also has potent antioxidant and anti-inflammatory properties, as described elsewhere herein, which further function to reduce the effects of aging.

Ketone body supplementation may also be associated with longevity promoting effects. As discussed above, ketone body supplementation can positively influence mitochondrial health, including raising the number of mitochondria and raising the concentration of antioxidants in the mitochondria to prevent reactive oxygen species (ROS) damage to the mitochondria. BHB may also stimulate chaperone-mediated autophagy of certain proteins marked by BHB oxidative modification (see Finn et al. "Ketone bodies stimulate chaperone-mediated autophagy" J. Biol. Chem. 2005 Jul. 8; 280(27): 25864-70).

The longevity promoting effects of CBD and exogenous ketone body supplementation are expected to be synergistically enhanced as a result of their combined administration. It is expected that the longevity effects of a ketonnabidiol composition will be greater than that possible with either component alone and/or will be greater than the sum of the effects of each component when used independently. Longevity is of course a multifaceted issue, and the longevity enhancing effects of ketonnabidiol supplementation may be further promoted by other beneficial effects described herein, such as neuroprotection, antioxidant effects, anti-inflammatory effects, cardiovascular health effects, and promotion of fat loss.

E. Anti-Inflammation/Analgesic

CBD provides an anti-inflammatory effect by modulating immune system functions of the ECS. Endocannabinoids, which are increased as a result of CBD administration, appear to serve an autoprotective role in ameliorating excessive inflammation (see, e.g., Pertwee "The pharmacology of cannabinoid receptors and their ligands: an overview" Int. J. Obes. (Lond.) (April 2006) 30 Suppl. 1: S13-8). CBD may also enhance the analgesic functions of certain endocannabinoids such as palmitoylethanolamide. CBD also inhibits the reuptake of the neurotransmitter adenosine, thereby acting to boost levels of adenosine in the brain. Adenosine receptors have broad ant-inflammatory effects.

Exogenous ketone body supplementation may also reduce inflammation, and in addition may induce ketosis and thereby further act to reduce inflammation. When under ketone body supplementation and/or when in ketosis, less insulin is produced, there is a reduction in inflammation markers, and there is a reduction in the generation of free radicals, which are known to contribute to inflammation. Ketone bodies also increase levels of adenosine, which is known to reduce inflammation and reduce pain. BHB also activates the AMPK pathway, which decreases inflammation and pain, and also inhibits the COX-2 enzyme in a manner somewhat similar to conventional non-steroidal anti-inflammatory drugs. BHB also inhibits the NLRP3 inflammasome, which is the pathway involved in initiating the inflammatory response.

BHB molecular signaling can further provide beneficial anti-inflammatory activity. For example, BHB molecular signaling may be associated with Class I and II histone deacetylase (HDAC) inhibition, which is related to inflammation control among other effects. BHB may also function to reduce expression of NALP3, which is a major component of the inflammasome. BHB may also increase gene expression of various endogenous defense proteins such as FOXO3 (tumor inhibitor), ROS scavengers such as catalase and SOD2, and toxic metal scavengers such as metallothionein. BHB may also act as an agonist of the $HCA_2$ protein. As with high-dose niacin supplementation, this is associated with anti-inflammatory effects in a variety of tissues including the brain, gastrointestinal tract, skin, and vascular tissue.

Although the anti-inflammatory properties discussed above may themselves lead to reductions in pain, the combined administration of CBD and ketone bodies is also expected to reduce perceptions of pain through one or more mechanisms independent of inflammation reduction. For example, CBD may bind to TRPV1 receptors in the brain, which are known to mediate pain perception.

It is expected that the anti-inflammatory and analgesic effects of CBD and ketone bodies are synergistically enhanced as a result of their combined administration. The ketone body component of the composition are expected to lead to reductions in inflammation by way of reduced reactive oxygen species and increased levels of adenosine, for example, and these effects may be further enhanced as a result of the ketone bodies inducing or sustain ketosis in the subject. The CBD component is meanwhile expected to further reduce excessive inflammation and pain through its modulation of the endocannabinoid system and inhibition of the reuptake of adenosine. It is expected that the resulting anti-inflammatory and analgesic effects will be greater than that possible with either component alone and/or will be greater than the sum of the effects of each component when used independently.

F. Anti-Tumorigenic

CBD supplementation may provide beneficial anti-tumorigenic effects through multiple mechanisms (see, e.g., Solinas et al. "Cannabidiol inhibits angiogenesis by multiple mechanisms" Br. J. Pharmacol. 2012 November; 167(6): 1218-31) (see also Massi et al. "Cannabidiol as potential anticancer drug" Br. J. Pharmacol. 2013 February; 75(2): 303-12).

Ketone body supplementation may also be associated with anti-tumorigenic effects. For example, BHB molecular signaling may increase gene expression of endogenous defense proteins such as FOXO3, which is a tumor inhibitor. Such supplementation may also increase the expression of other endogenous defense proteins such as catalase, SOD2, and toxic metal scavengers such as metallothionein. Enhanced levels of these proteins can reduce tumor incidence. The enhanced autophagy associated with ketone body supplementation can also limit the ability of tumors to take hold. Further, cancerous tumor cells are characterized by an increased glucose demand relative to normal, healthy cells, and thus are less able to effectively utilize ketone bodies for energy. A shift away from glucose as the primary cellular energy source and toward ketone bodies may therefore inhibit cancer progression (see, e.g., Poff et al. "Ketone supplementation decreases tumor cell viability and prolongs survival of mice with metastatic cancer" Int. J. Cancer 2014 Oct. 1; 135(7): 1711-20).

The anti-tumorigenic effects of CBD and exogenous ketone body supplementation are expected to be synergistically enhanced as a result of their combined administration. It is expected that the anti-tumorigenic effects of a ketonnabidiol composition will be greater than that possible with either component alone and/or will be greater than the sum of the effects of each component when used independently.

G. Anxiolytic/Anti-Depressant

A decrease in the endocannabinoid anandamide is believed to contribute to hypersecretion of the "stress hormone" corticosterone. CBD also appears to act as a positive allosteric modulator of the GABA-A receptor, enhancing the receptor's binding affinity for its principal agonist, GABA (see, e.g., Bakas et al. "The direct actions of cannabidiol and 2-arachidonoyl glycerol at $GABA_A$ receptors" Pharmacol. Res. 2017 May; 119:358-70). CBD may therefore reduce anxiety by enhancing the natural calming effects of GABA. CBD also appears to directly activate serotonin receptors in the brain, thereby conferring an anxiolytic and anti-depressant effect. Ketone bodies such as BHB and acetoacetate may also be involved in GABA receptor signaling, and may function synergistically with CBD to modulate GABA and/or GABA receptor activity.

Many individuals report a reduction in depressive symptoms as a result of a ketogenic diet, most likely due to general increases in physiological health. However, some individuals may experience an increase in symptoms of depression during ketosis because of difficulties in producing the neurotransmitter serotonin. Low serotonin levels are associated with depression and anxiety. Serotonin is derived from the essential amino acid tryptophan, which must be consumed in the diet. Tryptophan has a better likelihood of passing the blood-brain barrier, where it can be converted to serotonin, when it is at a higher blood concentration relative to other proteins and amino acids. When insulin is released, it functions to "pull" these other proteins and amino acids into muscles, leaving a higher proportion of tryptophan remaining in the blood to cross the blood-brain barrier. With a low-carb ketogenic diet, however, lower carbohydrate intake means less insulin is released. Thus, although a ketogenic diet includes an abundance of tryptophan, less tryptophan will cross the blood-brain barrier to be available for serotonin production because it must compete with other protein components in the blood.

The beneficial anxiolytic and anti-depressant effects of CBD can therefore complement the supplementation of exogenous ketone bodies by counteracting the potential negative effects related to low serotonin production. CBD readily crosses the blood-brain barrier and may therefore be available to maintain sufficient activation of serotonin receptors in the brain, even while a ketogenic diet is maintained.

BHB molecular signaling can further provide beneficial anxiolytic/anti-depressant activity. For example, BHB molecular signaling may be associated with Class I and II histone deacetylase (HDAC) inhibition, which has positive effects on mood, among other effects. BHB may also increase synthesis of gamma-Aminobutyric acid (GABA) in the brain, thereby promoting a calming, anxiolytic effect.

H. Cardiovascular Health

The endocannabinoids anandamide and N-arachidonoyl dopamine (NADA) act on temperature sensing TRPV1 channels. Activation of these channels can subsequently cause vasodilation, which can ease high blood pressure and promote good cardiovascular health. CBD supplementation can therefore enhance these effects of the ECS.

Exogenous ketone bodies may also aid in lowering blood pressure and/or improving cardiovascular health, and additionally may induce a sustained state of ketosis to further promote these effects. Ketosis can reduce the retention of sodium ions associated with high blood pressure. The lowered insulin release associated with ketosis may also correspond to reduced blood pressure.

BHB molecular signaling can further provide beneficial cardiovascular effects. For example, BHB may act as an agonist of the $HCA_2$ protein. As with high-dose niacin supplementation, this is associated with anti-inflammatory effects in a variety of tissues including vascular tissue. It is also associated with increasing levels of HDL cholesterol, reducing atherogenic activity, and promoting vasodilation.

It is expected that the cardiovascular effects of CBD and ketone bodies are synergistically enhanced as a result of their combined administration. The ketone body component of the composition is expected to lead to reductions in blood pressure and additionally may aid in inducing and sustaining ketosis in the subject to further promote these effects. The CBD component is meanwhile also expected to promote cardiovascular health through its modulation of the endocannabinoid system and/or activation of vasodilation channels. It is expected that the cardiovascular effects will be greater than that possible with either component alone and/or will be greater than the sum of the effects of each component independently.

I. Sleep Aid

Increased endocannabinoid signaling within the central nervous system can promote the induction of sleep. This may be a positive and desired effect in many circumstances. However, such drowsiness may in other circumstances be considered a nuisance side effect.

Supplementing with exogenous ketone bodies and/or inducing and maintaining a state of ketosis through exogenous ketone body supplementation can beneficially counteract CBD-induced drowsiness without disrupting circadian cycles or otherwise promoting insomnia. When the body is utilizing ketone bodies as an energy source, through exogenous ketone body supplementation or through ketosis induced/sustained by such supplementation, the energy supply is steadier and more consistent than the peaks and troughs typical of a state of glycolysis. This means that side effects of drowsiness associated with CBD may be offset by the efficient utilization of ketone bodies as a stable and consistent energy source.

IV. Dosage Forms and Administration

The ketonnabidiol composition may be administered in various ways including oral, intragastric, nasal or pulmonary, as an injectable (e.g., subdermal, parenteral, or intravenous), as a suppository, etcetera.

In some embodiments, the ketonnabidiol composition may be provided as a solid or powder form. Solid or powder ketogenic compositions may include one or more additional components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), phosphate salt (e.g., tricalcium phosphate), talcum, powdered cellulose, and the like.

In alternative embodiments, the ketonnabidiol composition may be provided as a liquid, such as in the form of a shot or mouth spray for fast delivery and absorption, or as a gel. Liquid or gel forms may include one or more carriers, such as water, ethanol, glycerin, propylene glycol, 1,3-propandiol, and the like, into which the components are dissolved or dispersed. The composition may include flavoring agents that help mask the somewhat poor taste of BHB compounds. These flavoring agents may include essential oils, such as peppermint, natural and artificial sweeteners, and other flavorants known in the art.

The ketonnabidiol composition may include one or more supplements known in the art, such as vitamins, minerals, and caffeine or other stimulants. For example, caffeine may be included in an amount of about 10 mg to about 250 mg, or about 25 mg to about 170 mg, or about 40 mg to about 120 mg.

The ketonnabidiol compositions described herein may be provided within a dosage regimen effective in inducing and sustaining ketosis and/or providing other benefits described herein. For example, the mass of exogenous ketone bodies in a daily dose (for an average adult of about 175 lbs.) may range from about 0.5 grams to about 50 grams, or about 1 gram to about 40 grams, or about 2 grams to about 30 grams, or about 3 grams to about 25 grams, or about 4 grams to about 20 grams, and may be provided using one or more unit doses. The mass of the CBD component in a daily dose (for an average adult of about 175 lbs.) may range from about 3 mg to 1 g, or about 10 mg to about 600 mg, or about 15 mg to about 400 mg, or about 20 mg to about 300 mg, and may be provided using one or more unit doses. As needed, dosages may be adjusted (e.g., linearly) based on weight of the subject. The CBD component and the ketone body component may be mixed/combined, though some methods may provide the components separately. The daily dose(s) may be taken as a single daily dose or as multiple doses (e.g., 2, 3, or 4 times daily).

In a preferred embodiment, a ketogenic composition is administered in one or more unit doses per day via oral administration of the composition in a solid, powdered form or liquid, such as in a powdered mixture (e.g., powder filled gelatin capsules), hard-pressed tablets, or other oral administration route known to those skilled in the art.

In some embodiments, multiple doses of the composition are administered. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etcetera.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo. In accordance with the present disclosure, a suitable single dose size is a dose that is capable of preventing or alleviating (reducing or eliminating) a symptom in a patient when administered one or more times over a suitable time period (e.g., a daily dose).

The amount of composition administered will depend on potency, absorption, distribution, metabolism, and excretion rates of the composition components, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once over a given time period (e.g., once per day), or may be divided and administered over intervals of time. It is to be understood that administration may be adjusted according to individual need and professional judgment of a person administrating or supervising the administration of the compositions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A composition comprising:
   a ketone body component;
   a cannabidiol (CBD) component, wherein the CBD component includes a CBD compound having at least one beta-hydroxybutyrate (BHB) or acetoacetate attached to the CBD compound via an ester bond; and a pharmaceutically or dietetically acceptable carrier.

2. The composition of claim 1, wherein the ketone body component is selected from the group consisting of BHB salts, BHB esters, beta-hydroxybutyric acid, acetoacetate salts, acetoacetate esters, acetoacetic acid, and combinations thereof.

3. The composition of claim 2, wherein the ketone body component includes a BHB salt or ester and/or acetoacetate salt or ester.

4. The composition of claim 1, wherein at least a portion of the ketone body component is provided by the CBD compound having at least one BHB or acetoacetate attached to the CBD compound via an ester bond.

5. The composition of claim 1, further comprising one or more additional cannabinoid compounds derived from the cannabis plant.

6. The composition of claim 1, wherein the composition omits THC.

7. The composition of claim 1, further comprising one or more of 1,3-butanediol, a fatty acid, or an ester of a fatty acid.

8. The composition of claim 7, wherein the fatty acid or ester thereof is a medium chain fatty acid or ester thereof, or a short chain fatty acid or ester thereof.

9. The composition of claim 1, wherein the composition is provided in solid or powder form.

10. The composition of claim 1, wherein the composition is provided in liquid form.

11. The composition of claim 1, wherein the composition is in a dosage form that provides from about 0.5 grams to about 50 grams of the ketone body component.

12. The composition of claim 1, wherein the composition is in a dosage form that provides about 3 mg to about 1 gram of the CBD component.

13. The composition of claim 1, wherein the composition promotes fat loss in a mammal.

14. The composition of claim 1, wherein the composition provides one or more of homeostasis promotion, appetite suppression, neuroprotection, memory enhancement, an anxiolytic effect, an anti-depressant effect, an anti-inflammation effect, an analgesic effect, an antioxidant effect, blood pressure and/or heart rate modulation, an anti-tumorigenic effect, a longevity promoting effect, and sleep promotion.

15. The composition of claim 1, wherein the CBD component functions to counteract serotonin reduction associated with administration of the ketone body component.

16. The composition of claim 1, wherein the composition promotes fat browning in the mammal and increases the effectiveness of lipolysis.

17. The composition of claim 1, wherein the composition accelerates the production of endogenous ketones.

18. The composition of claim 1, wherein the ketone body component increases the pharmacokinetic utilization of the CBD component relative to pharmacokinetic utilization of the CBD component in the absence of the ketone body component.

19. The composition of claim 1, wherein the composition induces sustained ketosis in the mammal with reduced symptoms of hypoglycemia relative to a ketone body composition omitting CBD.

20. The composition of claim 1, wherein the ketone body component includes BHB and/or acetoacetate, and wherein the BHB and/or acetoacetate enhances effectiveness of the composition at least in part as a result of molecular signaling.

21. The composition of claim 1, wherein the composition enhances function of the endocannabinoid system in a mammal.

22. A composition comprising:
   a cannabidiol (CBD) compound having at least one beta-hydroxybutyrate (BHB) or acetoacetate attached to the CBD compound via an ester bond; and
   a pharmaceutically or dietetically acceptable carrier.

23. The composition of claim 22, further comprising a CBD component separate from the CBD compound having at least one BHB or acetoacetate attached to the CBD compound via an ester bond.

24. The composition of claim 22, further comprising a ketone body component separate from the CBD compound having at least one BHB or acetoacetate attached to the CBD compound via an ester bond.

* * * * *

UNITED STATES PATENT AND TRADEMARK OFFICE
CERTIFICATE OF CORRECTION

PATENT NO. : 10,512,615 B1
APPLICATION NO. : 16/272359
DATED : December 24, 2019
INVENTOR(S) : Gary Millet Page 1 of 1

It is certified that error appears in the above-identified patent and that said Letters Patent is hereby corrected as shown below:

On the Title Page

Page 2
Item (56), References Cited, change "Krotkiewski, M. "Value of VLCD Supplementation with Medium Chain Triglycerides." I'nt JobesRelatMetab Disord. Sep. 2001; 25(9):1 393/\00." to –Krotkiewski, M. "Value of VLCD Supplementation with Medium Chain Triglycerides." I'nt JobesRelatMetab Disord. Sep. 2001; 25(9):1393-1400–

In the Specification

Column 1
Line 60, change "entering" to –enter–

Column 4
Line 45, change "compounds" to –compound–

Column 6
Line 40, change "produces" to –produce–

Column 10
Line 6, change "manufacture" to –manufactured–

Column 19
Line 5, change "are" to –is–

Signed and Sealed this
Sixteenth Day of June, 2020

Andrei Iancu
*Director of the United States Patent and Trademark Office*